US010687759B2

(12) United States Patent
Guo et al.

(10) Patent No.: US 10,687,759 B2
(45) Date of Patent: Jun. 23, 2020

(54) SHIELDING TECHNIQUES FOR NOISE REDUCTION IN SURFACE ELECTROMYOGRAPHY SIGNAL MEASUREMENT AND RELATED SYSTEMS AND METHODS

(71) Applicant: Facebook Technologies, LLC, Menlo Park, CA (US)

(72) Inventors: Ning Guo, Brooklyn, NY (US); Alexandre Barachant, Brooklyn, NY (US); Jonathan Reid, Brooklyn, NY (US)

(73) Assignee: Facebook Technologies, LLC, Menlo Park, CA (US)

(*) Notice: Subject to any disclaimer, the term of this patent is extended or adjusted under 35 U.S.C. 154(b) by 0 days.

(21) Appl. No.: 16/424,144

(22) Filed: May 28, 2019

(65) Prior Publication Data

US 2019/0365318 A1 Dec. 5, 2019

Related U.S. Application Data

(60) Provisional application No. 62/696,242, filed on Jul. 10, 2018, provisional application No. 62/677,574, filed on May 29, 2018.

(51) Int. Cl.
*A61B 5/00* (2006.01)
*H05K 9/00* (2006.01)
(Continued)

(52) U.S. Cl.
CPC .......... *A61B 5/681* (2013.01); *A61B 5/0488* (2013.01); *H05K 9/0007* (2013.01);
(Continued)

(58) Field of Classification Search
CPC ................ H05K 9/007; A61B 2562/182
See application file for complete search history.

(56) References Cited

U.S. PATENT DOCUMENTS 4,055,168 A * 10/1977 Miller ............... A61B 5/103
600/594
4,896,120 A 1/1990 Kamil
(Continued)

FOREIGN PATENT DOCUMENTS

CA 2902045 A1 8/2014
CA 2921954 A1 2/2015
(Continued)

OTHER PUBLICATIONS

Extended European Search Report for European Application No. EP 17835111.0 dated Nov. 21, 2019.
(Continued)

*Primary Examiner* — Hung V Ngo
(74) *Attorney, Agent, or Firm* — FisherBroyles, LLP

(57) ABSTRACT

Techniques for shielding wearable surface electromyography (sEMG) devices are described. According to some aspects, an sEMG device may comprise amplification circuitry comprising at least a first differential amplifier and at least two sEMG electrodes electrically connected to the amplification circuitry. The device may further comprise at least one auxiliary conductor not electrically connected to the amplification circuitry, wherein the at least one auxiliary conductor is configured to be electrically coupled to a wearer of the wearable device, and an electromagnetic shield surrounding the wearable device at least in part and electrically connected to the at least one auxiliary conductor.

14 Claims, 7 Drawing Sheets

(51) Int. Cl.
*A61B 5/0488* (2006.01)
*H03F 3/45* (2006.01)

(52) U.S. Cl.
CPC ... *A61B 2562/043* (2013.01); *A61B 2562/182* (2013.01); *H03F 3/45475* (2013.01)

(56) References Cited

U.S. PATENT DOCUMENTS

| | | |
|---|---|---|
| 5,625,577 A | 4/1997 | Kunii et al. |
| 6,005,548 A | 12/1999 | Latypov et al. |
| 6,009,210 A | 12/1999 | Kand |
| 6,244,873 B1 | 6/2001 | Hill et al. |
| 6,411,843 B1 | 6/2002 | Zarychta |
| 6,658,287 B1 | 12/2003 | Litt et al. |
| 6,720,984 B1 | 4/2004 | Jorgensen et al. |
| 6,774,885 B1 | 8/2004 | Even-Zohar |
| 6,942,621 B2 | 9/2005 | Avinash et al. |
| 7,089,148 B1 | 8/2006 | Bachmann et al. |
| 7,351,975 B2 | 4/2008 | Brady et al. |
| 7,574,253 B2 | 8/2009 | Edney et al. |
| 7,580,742 B2 | 8/2009 | Tan et al. |
| 7,787,946 B2 | 8/2010 | Stahmann et al. |
| 7,805,386 B2 | 9/2010 | Greer |
| 7,901,368 B2 | 3/2011 | Flaherty et al. |
| 8,170,656 B2 | 5/2012 | Tan et al. |
| 8,190,249 B1 | 5/2012 | Gharieb et al. |
| 8,311,623 B2 | 11/2012 | Sanger |
| 8,351,651 B2 | 1/2013 | Lee |
| 8,421,634 B2 | 4/2013 | Tan et al. |
| 8,435,191 B2 | 5/2013 | Barboutis et al. |
| 8,437,844 B2 | 5/2013 | Syed Momen et al. |
| 8,447,704 B2 | 5/2013 | Tan et al. |
| 8,484,022 B1 | 7/2013 | Vanhoucke |
| 8,718,980 B2 | 5/2014 | Garudadri et al. |
| 8,744,543 B2 | 6/2014 | Li et al. |
| 8,754,862 B2 | 6/2014 | Zaliva |
| D717,685 S | 11/2014 | Bailey et al. |
| 8,880,163 B2 | 11/2014 | Barachant et al. |
| 8,890,875 B2 | 11/2014 | Jammes et al. |
| 8,892,479 B2 | 11/2014 | Tan et al. |
| 9,037,530 B2 | 5/2015 | Tan et al. |
| D742,272 S | 11/2015 | Bailey et al. |
| 9,218,574 B2 | 12/2015 | Phillipps et al. |
| 9,235,934 B2 | 1/2016 | Mandella et al. |
| 9,240,069 B1 | 1/2016 | Li |
| 9,278,453 B2 | 3/2016 | Assad |
| 9,299,248 B2 | 3/2016 | Lake et al. |
| D756,359 S | 5/2016 | Bailey et al. |
| 9,351,653 B1 | 5/2016 | Harrison |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,408,316 B2 | 8/2016 | Bailey et al. |
| 9,459,697 B2 | 10/2016 | Bedikian et al. |
| 9,483,123 B2 | 11/2016 | Aleem et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 2003/0144829 A1 | 7/2003 | Geatz et al. |
| 2003/0171921 A1 | 9/2003 | Manabe et al. |
| 2003/0184544 A1 | 10/2003 | Prudent |
| 2004/0054273 A1 | 3/2004 | Finneran et al. |
| 2004/0092839 A1 | 5/2004 | Shin et al. |
| 2006/0129057 A1 | 6/2006 | Maekawa et al. |
| 2007/0009151 A1 | 1/2007 | Pittman et al. |
| 2007/0172797 A1 | 7/2007 | Hada et al. |
| 2007/0177770 A1 | 8/2007 | Derchak et al. |
| 2007/0256494 A1 | 11/2007 | Nakamura et al. |
| 2007/0285399 A1 | 12/2007 | Lund |
| 2008/0051673 A1 | 2/2008 | Kong et al. |
| 2008/0052643 A1 | 2/2008 | Ike et al. |
| 2008/0103639 A1 | 5/2008 | Troy et al. |
| 2008/0214360 A1 | 9/2008 | Stirling et al. |
| 2008/0221487 A1 | 9/2008 | Zohar et al. |
| 2009/0027337 A1 | 1/2009 | Hildreth |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0112080 A1 | 4/2009 | Matthews |
| 2009/0124881 A1* | 5/2009 | Rytky .................. A61B 5/0408 600/388 |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0063794 A1 | 3/2010 | Hernandez-Rebollar |
| 2010/0106044 A1 | 4/2010 | Linderman |
| 2010/0113910 A1 | 5/2010 | Brauers et al. |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0315266 A1 | 12/2010 | Gunawardana et al. |
| 2011/0077484 A1 | 3/2011 | Van Slyke et al. |
| 2011/0092826 A1 | 4/2011 | Lee et al. |
| 2011/0173204 A1 | 7/2011 | Murillo et al. |
| 2011/0173574 A1 | 7/2011 | Clavin et al. |
| 2011/0230782 A1 | 9/2011 | Bartol et al. |
| 2012/0066163 A1 | 3/2012 | Balls et al. |
| 2012/0188158 A1 | 7/2012 | Tan et al. |
| 2012/0265480 A1 | 10/2012 | Oshima |
| 2012/0283526 A1 | 11/2012 | Gommesen et al. |
| 2013/0004033 A1 | 1/2013 | Trugenberger |
| 2013/0077820 A1 | 3/2013 | Marais et al. |
| 2013/0123656 A1 | 5/2013 | Heck |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1 | 9/2013 | Tan et al. |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |

(56) References Cited

U.S. PATENT DOCUMENTS

| | | |
|---|---|---|
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0182165 A1 | 7/2015 | Miller et al. |
| 2015/0193949 A1 | 7/2015 | Katz et al. |
| 2015/0223716 A1* | 8/2015 | Korkala ............... A61B 5/0245 600/393 |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0092504 A1 | 3/2016 | Mitri et al. |
| 2016/0144172 A1 | 5/2016 | Hsueh et al. |
| 2016/0162604 A1 | 6/2016 | Xiaoli et al. |
| 2016/0187992 A1 | 6/2016 | Yamamoto et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1* | 10/2017 | Nguyen ............... H01Q 1/2283 |
| 2017/0308118 A1 | 10/2017 | Ito |
| 2017/0344706 A1 | 11/2017 | Torres et al. |
| 2017/0347908 A1 | 12/2017 | Watanabe et al. |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1 | 4/2018 | Kerth et al. |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0324549 A1 | 10/2019 | Araki et al. |
| 2019/0357787 A1 | 11/2019 | Barachant et al. |
| 2019/0362557 A1 | 11/2019 | Lacey et al. |

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |

(56) References Cited

FOREIGN PATENT DOCUMENTS

| | | |
|---|---|---|
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2010/104879 A2 | 9/2010 |
| WO | WO 2012/155157 A1 | 11/2012 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |
| WO | WO 2017/208167 A1 | 12/2017 |

OTHER PUBLICATIONS

Extended European Search Report for European Application No. EP 17835140.9 dated Nov. 26, 2019.
International Search Report and Written Opinion for International Application No. PCT/US2019/037302 dated Oct. 11, 2019.
International Search Report and Written Opinion for International Application No. PCT/US2019/034173 dated Sep. 18, 2019.
International Search Report and Written Opinion for International Application No. PCT/US2019/042579 dated Oct. 31, 2019.
Invitation to Pay Additional Fees for International Application No. PCT/US2019/049094 dated Oct. 24, 2019.
International Search Report and Written Opinion for International Application No. PCT/US2019/052131 dated Dec. 6, 2019.
International Search Report and Written Opinion for International Application No. PCT/US2019/046351 dated Nov. 7, 2019.
Al-Mashhadany, Inverse Kinematics Problem (IKP) of 6-DOF Manipulator Bgy Locally Recurrent Neural Networks (LRNNs). Management and Service Science (MASS). 2010 International Conference on, IEEE. Aug. 24, 2010. 5 pages. ISBN: 978-1-4244-5325-2.
Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.
Marcard et al., Sparse Inertial Poser: Automatic 3D Human Pose Estimation from Sparse IMUs. Eurographics. 2017;36(2). 12 pages.
Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].
Wittevrongel et al., Spatiotemporal Beamforming: A Transparent and Unified Decoding Approach to Synchronous Visual Brain-Computer Interfacing. Frontiers in Neuroscience. 2017;11:1-12.
Zacharaki et al., Spike pattern recognition by supervised classification in low dimensional embedding space. Brain Informatics. 2016;3:73-8. DOI: 10.1007/s40708-016-0044-4.
International Search Report and Written Opinion for International Application No. PCT/US2017/043686 dated Oct. 6, 2017.
International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US2019/028299 dated Aug. 9, 2019.
Invitation to Pay Additional Fees for International Application No. PCT/US2019/031114 dated Aug. 6, 2019.
International Search Report and Written Opinion for International Application No. PCT/US19/20065 dated May 16, 2019.
Arkenbout et al., Robust Hand Motion Tracking through Data Fusion of 5DT Data Glove and Nimble VR Kinect Camera Measurements. Sensors. 2015;15:31644-71.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Davoodi et al., Development of a Physics-Based Target Shooting Game to Train Amputee Users of Multijoint Upper Limb Protheses. Presence. Massachusetts Institute of Technology. 2012;21(1):85-95.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Gallina et al., Surface EMG Biofeedback. Surface Electromyography: Physiology, Engineering, and Applications. 2016:485-500.

(56) References Cited

OTHER PUBLICATIONS

Gopura et al., A Human Forearm and wrist motion assist exoskeleton robot with EMG-based fuzzy-neuro control. Proceedings of the 2nd IEEE/RAS-EMBS International Conference on Biomedial Robotics and Biomechatronics. Oct. 19-22, 2008. 6 pages.
Hauschild et al., A Virtual Reality Environment for Designing and Fitting Neural Prosthetic Limbs. IEEE Transactions on Neural Systems and Rehabilitation Engineering. 2007;15(1):9-15.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Lee et al., Motion and Force Estimation System of Human Fingers. Journal of Institute of Control, Robotics and Systems. 2011;17(10):1014-1020.
Li et al., Motor Function Evaluation of Hemiplegic Upper-Extremities Using Data Fusion from Wearable Inertial and Surface EMG Sensors. Sensors. MDPI. 2017;17(582):1-17.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
McIntee, A Task Model of Free-Space Movement-Based Geastures. Dissertation. Graduate Faculty of North Carolina State University. Computer Science. 2016. 129 pages.
Mendes et al., Sensor Fusion and Smart Sensor in Sports and Biomedical Applications. Sensors. 2016;16(1569):1-31.
Naik et al., Source Separation and Identification issues in bio signals: A solution using Blind source seperation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sartori et al., Neural Data-Driven Musculoskeletal Modeling for Personalized Neurorehabilitation Technologies. IEEE Transactions on Biomedical Engineering. 2016;63(5):879-93.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Valero-Cuevas et al., Computational Models for Neuromuscular Function. NIH Public Access Author Manuscript. Jun. 16, 2011. 52 pages.
Wodzinski et al., Sequential Classification of Palm Gestures Based on a* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
Yang et al., Surface EMG based handgrip force predictions using gene expression programming. Neurocomputing. 2016;207:568-579.

\* cited by examiner

SHIELDING TECHNIQUES FOR NOISE REDUCTION IN SURFACE ELECTROMYOGRAPHY SIGNAL MEASUREMENT AND RELATED SYSTEMS AND METHODS

CROSS-REFERENCE TO RELATED APPLICATIONS

The present application claims the benefit under 35 U.S.C. § 119(e) of U.S. Provisional Patent Application No. 62/677,574, filed May 29, 2018, titled "Techniques for Shielding Surface Electromyography Signals and Related Systems and Methods," and U.S. Provisional Patent Application No. 62/696,242 filed Jul. 10, 2018, titled "Shielding Techniques for Noise Reduction in Surface Electromyography Signal Measurement and Related Systems And Methods," each of which is hereby incorporated by reference in its entirety.

BACKGROUND

Surface electromyography (sEMG) is a process that involves the detection of electrical activity produced by one or more groups of muscles, at rest and/or during activity. High quality sEMG signals are typically acquired from wet electrodes in a laboratory setting using skin preparations that require application of a gel or paste at the electrode-skin interface to improve the conductivity between the skin and the electrodes. In wireless communication applications, shielding is typically used to reduce radio-frequency interference and it is normally implemented by covering all or portions of the circuit with shielding material connected to the ground plane.

SUMMARY

According to some aspects, a wearable device is provided comprising amplification circuitry comprising at least a first differential amplifier, at least two sEMG electrodes electrically connected to the amplification circuitry, at least one auxiliary conductor not electrically connected to the amplification circuitry, wherein the at least one auxiliary conductor is configured to be electrically coupled to a wearer of the wearable device, and an electromagnetic shield surrounding the wearable device at least in part and electrically connected to the at least one auxiliary conductor.

According to some aspects, a method of attenuating noise in a wearable device is provided, the wearable device comprising amplification circuitry, at least two sEMG electrodes electrically connected to inputs of the amplification circuitry, and an electromagnetic shield surrounding the wearable device at least in part, the method comprising electrically coupling the at least two sEMG electrodes to a wearer of the wearable device, and electrically coupling the electromagnetic shield to the wearer without electrically coupling the electromagnetic shield to the amplification circuitry except via the wearer and via air between the electromagnetic shield and the amplification circuitry.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Figure 1:
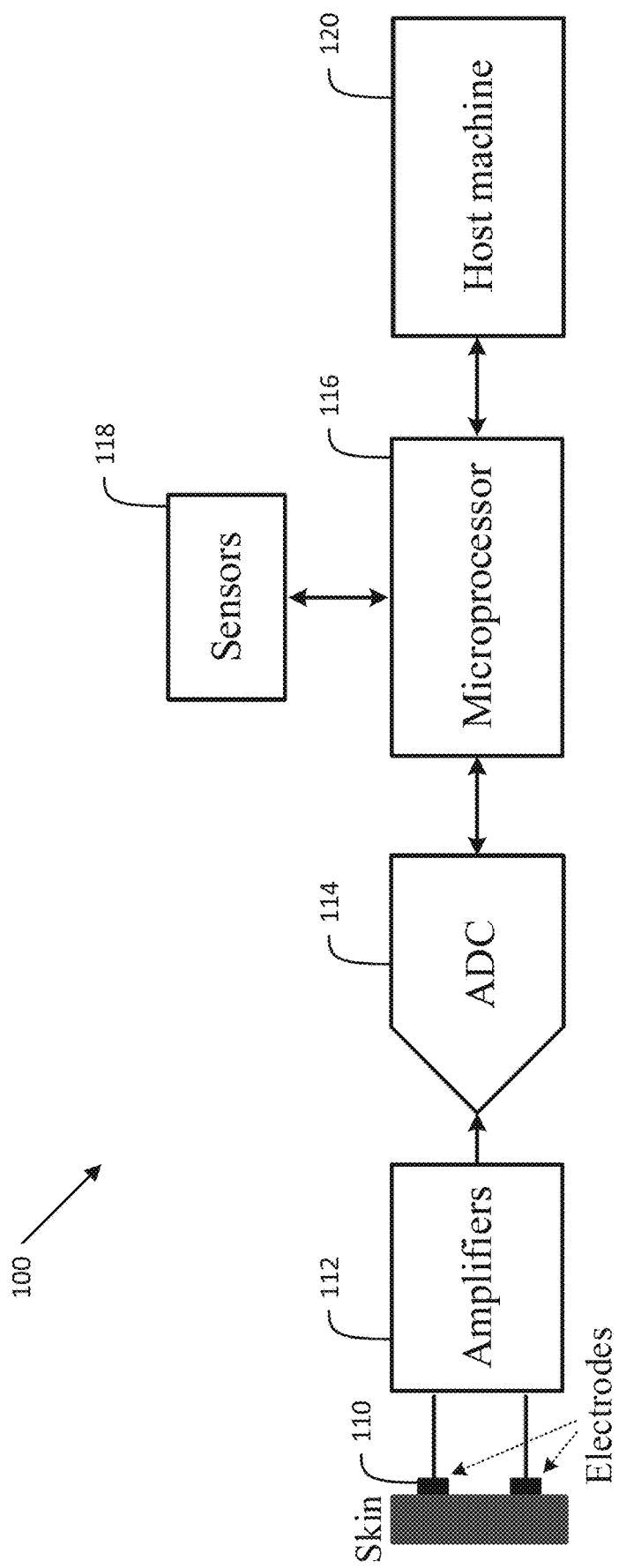
FIG. 1 is a schematic diagram of components of an sEMG system in accordance with some embodiments of the technology described herein.

Obtaining consistent high-quality sEMG signals using sEMG electrodes and conventional signal conditioning and processing techniques is challenging, in part due to the low voltages produced by muscle fibers. Moreover, obtaining high-quality sEMG signals from dry sEMG electrodes is generally more challenging than with wet sEMG electrodes, because wet sEMG electrodes generally have a lower impedance conductive path between the electrode and the skin via an intervening gel. With dry sEMG electrodes, however, there may be various low conductivity materials between the electrode and the skin, such as air, body hair and/or moisture, resulting in inconsistent electrode signals that may exhibit considerable noise. For applications that require near real-time analysis of sEMG signals with dry electrodes, the acquisition of consistent high-quality signals with reliable devices is important, both from a user experience perspective and from a development perspective. As referred to herein, sEMG signals are signals produced by one or more sEMG electrodes, and are typically produced by the electrodes in response to electrical signals produced by one or more muscles or groups of muscles.

The inventors have recognized and appreciated that sEMG signals are low amplitude in nature (e.g., in the range of several $\mu V$ to several mV) and particularly susceptible to external noise sources, which can capacitively couple through the air to a circuit containing sEMG electrodes. For instance, external noise may couple through the air to inputs of an sEMG data acquisition system, particularly in the case of high impedance inputs. External sources of noise may include, for example, AC power lines and AC-powered devices, which may produce sources of 50 Hz or 60 Hz noise. While the capacitance of the air is comparatively small (e.g., on the order of femtofarads), the voltages of sEMG signals may be sufficiently low such that even a heavily attenuated source of external noise can produce a signal that interferes with accurate measurement of the sEMG signals.

The inventors have further recognized and appreciated that conventional approaches to shielding circuits function poorly in sEMG devices (that is, a device that includes one or more sEMG electrodes). For instance, conventional shielding techniques typically place a conductor around a circuit and directly connect the conductor to the circuit ground or some other well-defined potential. It has been observed by the inventors, however, that such an approach does not appreciably suppress signals produced within an sEMG device by external sources of noise, and in some cases may even increase the amount of noise in the sEMG signals.

Some embodiments are directed to techniques for suppressing signals produced within an sEMG device by external sources of noise by electrically coupling a shielding structure to the skin of the wearer of a wearable device that includes sEMG sensors arranged thereon. The shielding structure acts to substantially suppress signals produced within an sEMG device by external sources of noise. Such suppression of noise may occur even though the body of the wearer provides a ground that is generally not well-defined, nor necessarily at a stable potential.

FIG. 1 schematically depicts components of an illustrative sEMG system 100, in accordance with some embodiments. System 100 includes a pair of sEMG electrodes 110, which may include any combination of wet and/or dry sEMG electrodes. In some embodiments, electrodes 110 may be arranged as a portion of a wearable device configured to be worn on or around part of a user's body. For example, in one non-limiting example, a plurality of sEMG sensors including sEMG electrodes (e.g., electrodes 110) are arranged circumferentially around an adjustable and/or elastic band such as a wristband or armband configured to be worn around a user's wrist or arm. Alternatively, at least some of the sEMG sensors may be arranged on a wearable patch configured to be affixed to a portion of the user's body.

In some embodiments, the sEMG electrodes may be minimally invasive and may include one or more conductive components placed in or through all or part of the dermis of the user. In at least some cases of the above-described arrangement, the resulting EMG signals may not, in a strict technical sense, be considered "surface" EMG signals. Nonetheless, reducing external sources of noise is also a fundamental challenge for minimally invasive EMG recordings.

Figure 2:
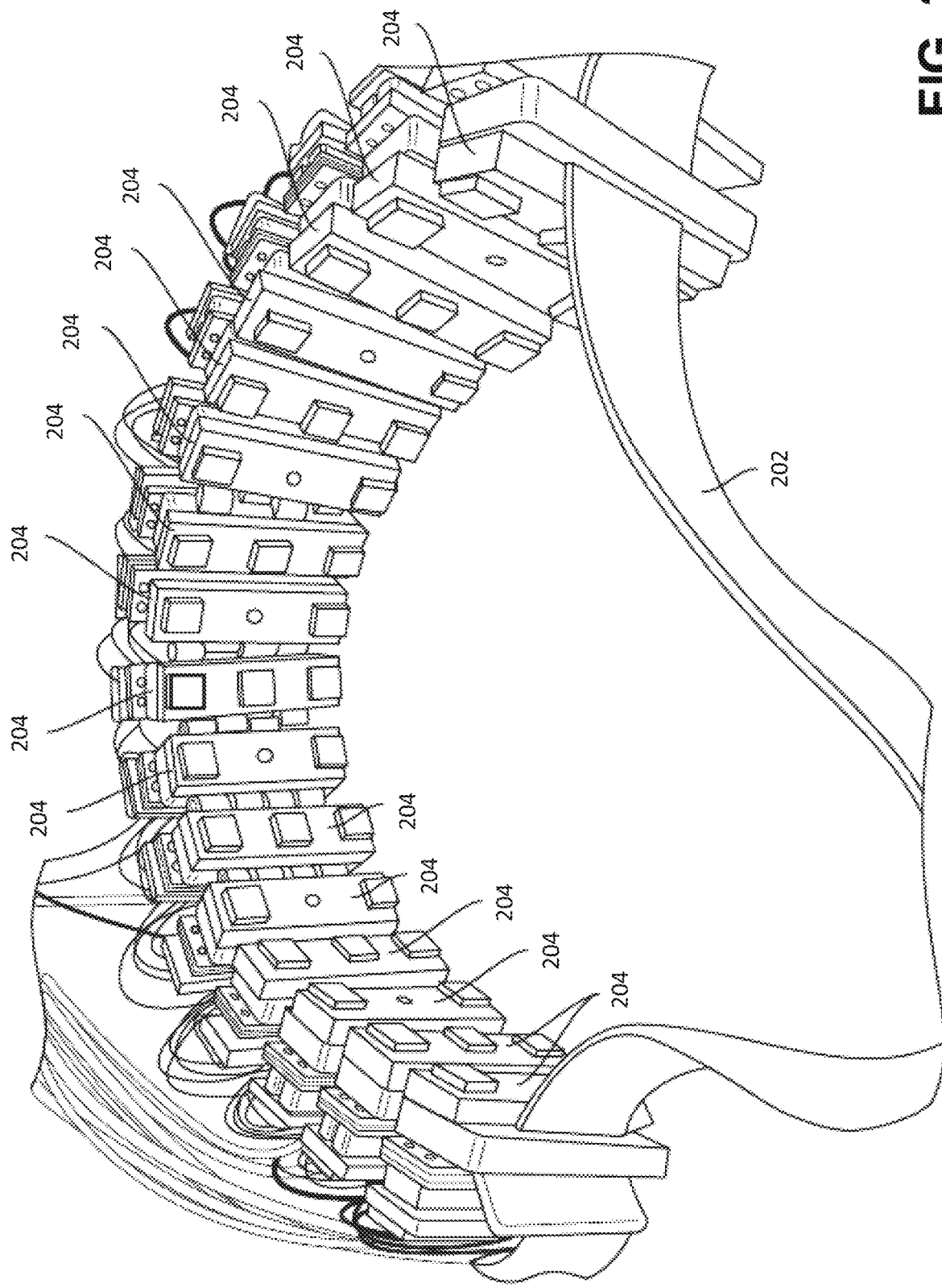
FIG. 2 illustrates a wristband having sEMG sensors arranged circumferentially thereon, in accordance with some embodiments of the technology described herein.
Figure 3:
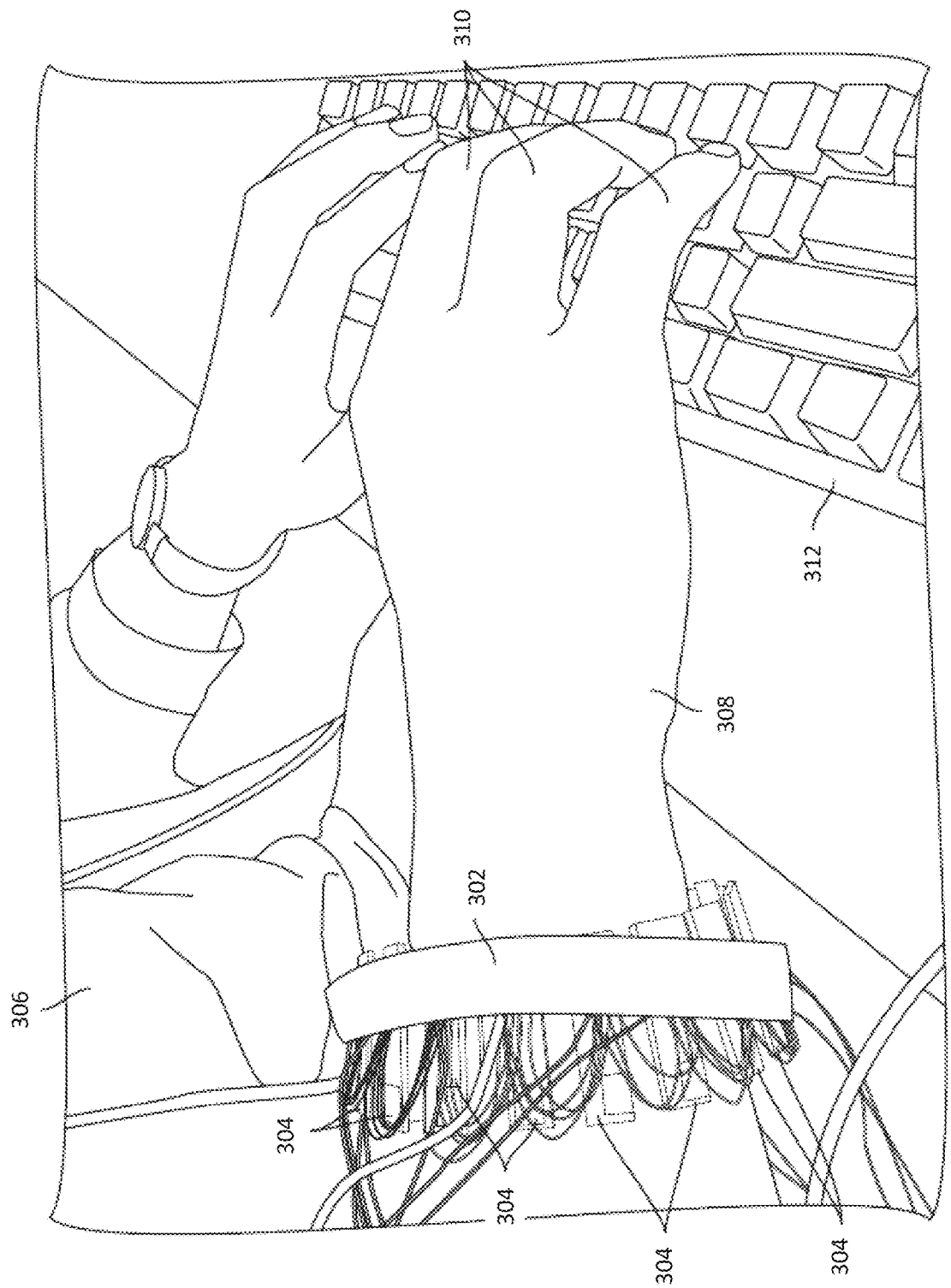
FIG. 3 illustrates a user wearing the wristband of FIG. 2 while typing on a keyboard, in accordance with some embodiments of the technology described herein.
Figure 4:
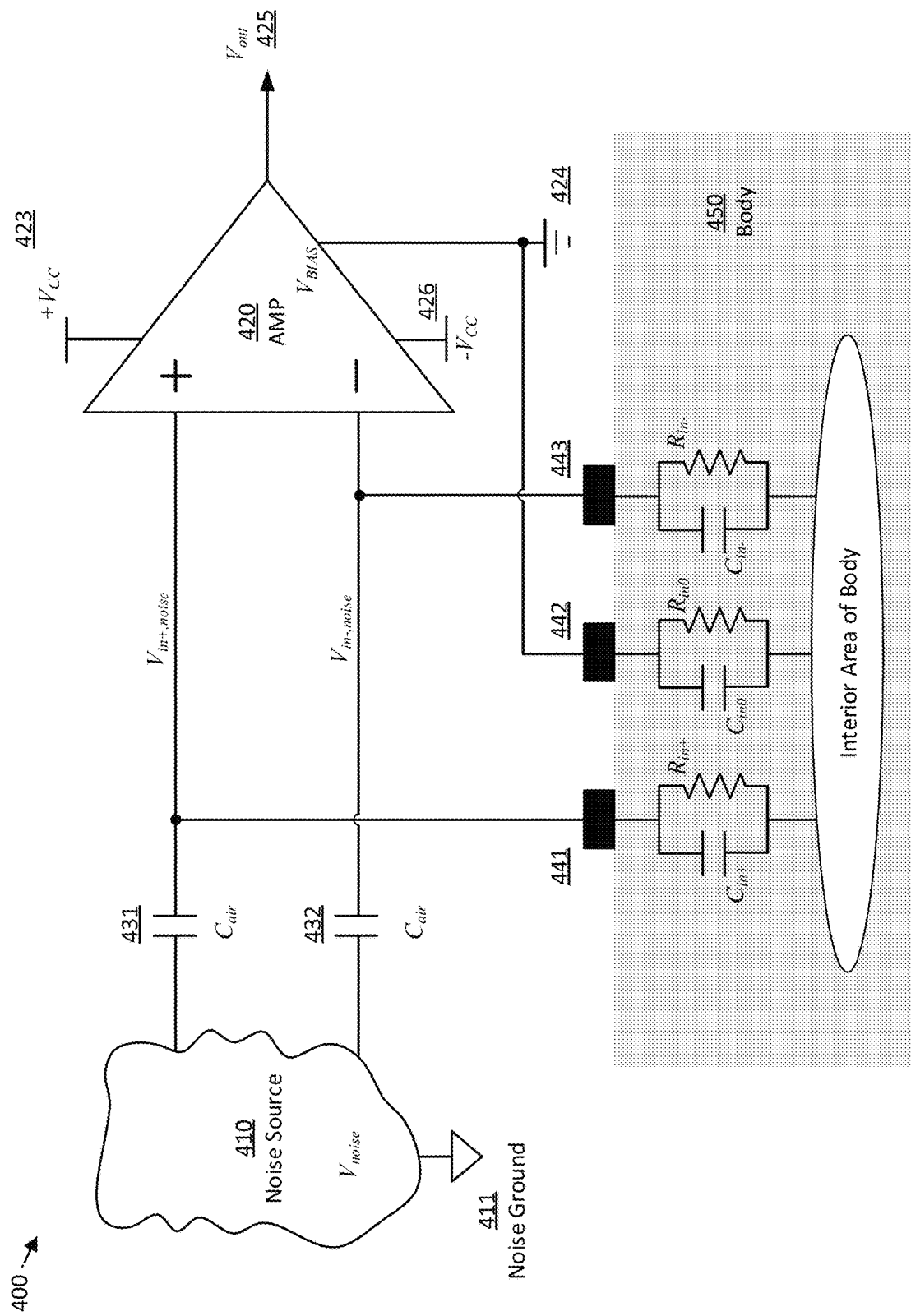
FIG. 4 depicts an illustrative amplifier of an sEMG device, according to some embodiments.
Figure 5:
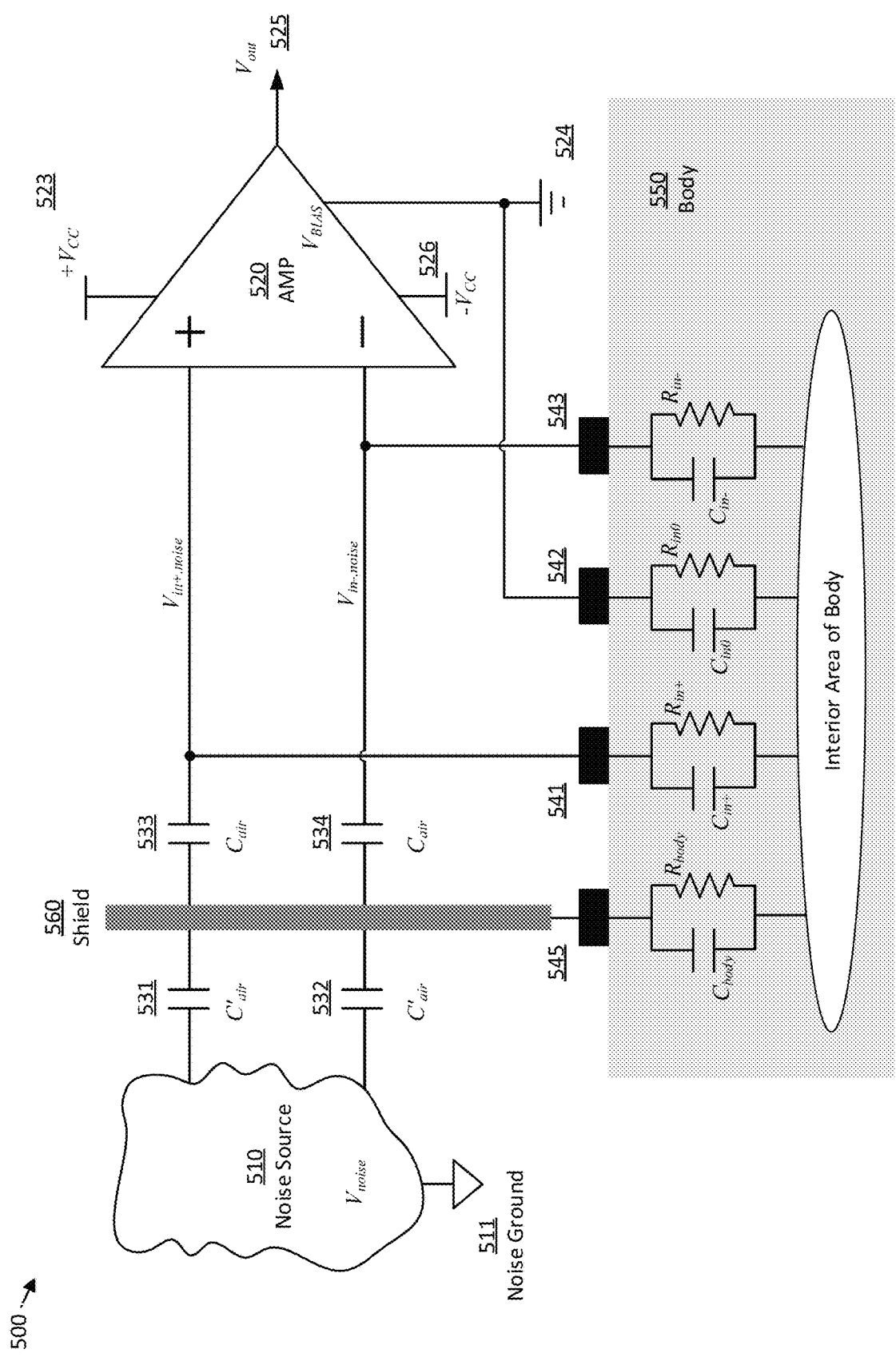
FIG. 5 depicts an illustrative amplifier of an sEMG device in which a shield mitigates interference produced by sources of external noise, according to some embodiments.

In one implementation, sixteen sEMG sensors including sEMG electrodes are arranged circumferentially around an elastic band configured to be worn around a user's lower arm. For example, FIG. 2 shows sEMG sensors 204 arranged circumferentially around elastic band 202. It should be appreciated that any suitable number of sEMG sensors having any suitable number of sEMG electrodes (including wet and/or dry sEMG electrodes) may be used and the number and arrangement of sensors/electrodes may depend on the particular application for which the wearable device is used. For example, as shown in FIG. 2, some of the sEMG sensors 204 include two sEMG electrodes, whereas others of the sEMG sensors 204 include three sEMG electrodes, with the middle of the three electrodes being a ground electrode. The ground electrode may be included on one or more of the sEMG sensors 204 to, for example, further bias the skin potential and/or to filter out noise. Although the schematic diagrams in FIGS. 1, 4 and 5 illustrate only two or three electrodes being connected to an amplifier, it should be appreciated that for sEMG sensors 204 in which three (or more) electrodes are used, a corresponding number of connections between the electrodes and the amplification circuitry would be included. In one example application of the technology described herein, FIG. 3 shows a user 306 wearing elastic band 302 on hand 308. In this way, sEMG sensors 304 may be configured to record sEMG signals as a user controls keyboard 312 using fingers 310.

Surface potentials recorded by sEMG electrodes are typically small and amplification of the signals recorded by the sEMG electrodes is typically desired. As shown in FIG. 1, sEMG electrodes 110 are coupled to amplification circuitry 112, configured to amplify the sEMG signals recorded by the electrodes. The output of the amplification circuitry 112 is provided to analog-to-digital converter (ADC) circuitry 114, which converts the amplified sEMG signals to digital signals for further processing by microprocessor 116. Microprocessor 116 may be implemented by one or more hardware processors. The processed signals output from microprocessor 116 may be interpreted by host machine 120, examples of which include, but are not limited to, a desktop computer, a laptop computer, a smartwatch, a smartphone, or any other computing device. In some implementations, host machine 120 may be configured to output one or more control signals for controlling a physical or virtual device based, at least in part, on an analysis of the signals output from microprocessor 116.

As shown, sEMG system 100 also includes sensors 118, which may be configured to record types of information about a state of a user other than sEMG information. For example, sensors 118 may include, but are not limited to, temperature sensors configured to measure skin/electrode temperature, inertial measurement unit (IMU) sensors configured to measure movement information such as rotation and acceleration, humidity sensors, heart-rate monitor sensors, and other bio-chemical sensors configured to provide information about the user and/or the user's environment.

One illustrative implementation of amplification circuitry 112 shown in FIG. 1 is illustrated in FIG. 4, according to some embodiments. In the example of the sEMG device 400 shown in FIG. 4, sEMG electrodes 441, 442 and 443 (which are, for example, instances of electrodes 110 shown in FIG. 1, and which may include any combination of wet and/or dry sEMG electrodes) are electrically coupled to a user's body 450. Due to the nature of contact afforded by sEMG electrodes, the coupling between each of the electrodes 441, 442, 443 and the body 450 is associated with resistances $R_{in+}$, $R_{in0}$, $R_{in-}$, respectively, and capacitances $C_{in+}$, $C_{in0}$, $C_{in-}$, respectively. The values of these resistances and capacitances may be expected to vary between the electrodes due to, for example, one or more of: variation in skin conditions (e.g., hydration levels, amounts of intervening body hair), differing amounts of physical contact between the respective electrode and skin, and/or manufacturing variations between electrodes 441, 442 and 443.

In the example of FIG. 4, signals sensed by the electrodes 441 and 443 are provided to inputs of the differential amplifier 420, which is powered using a dual power supply with voltage $+V_{CC}$ (423) as a positive supply and voltage $-V_{CC}$ (426) as a negative supply with respect to ground (424). An amplified signal produced by the amplifier 420 is output at 425. Electrode 442 is connected to circuit ground 424. In at least some cases, the connection of electrode 442 to circuit ground 424 may act to bias the body 450; for example, the connection may stabilize the body DC potential at circuit ground.

As discussed above, in some cases external noise sources can couple through the air to sEMG devices. For instance, in the example of FIG. 4, the noise source 410 may couple to the inputs of the amplifier circuit through the air, represented in FIG. 4 by the capacitors 431 and 432 which represent the parasitic capacitance between noise source 410 and inputs of amplifier 420. Unwanted noise may thereby be produced in output 425.

For example, based on the illustrated parasitic capacitances of the air and amplifier inputs from electrodes 441 and 443 shown in FIG. 4, and ignoring the resistances $R_{in+}$, $R_{in0}$, $R_{in-}$ for simplicity, the voltage signals that the noise source 410 produces as input to the amplifier 420 may be expressed as:

$$V_{in+,noise} = \left(\frac{C_{air}}{C_{air} + C_{in+}}\right) \times V_{noise} \quad \text{(Eqn. 1)}$$

$$V_{in-,noise} = \left(\frac{C_{air}}{C_{air} + C_{in-}}\right) \times V_{noise} \quad \text{(Eqn. 2)}$$

where $V_{noise}$ is the noise signal produced by the noise source 410 (e.g., a 60 Hz signal produced by an AC power cable and/or AC-powered device). Note that the voltages $V_{in+,noise}$ and $V_{in-,noise}$ are voltage signals input to the amplifier 420 in addition to sEMG voltage signals sensed by the electrodes 441 and 443 from the body 450. Moreover, it should be appreciated that in some cases the capacitance of the air may not be identical in each of the above equations due to minor differences in distance between the noise source and the amplifier, but is treated as so for simplicity.

As Eqns. 1 and 2 illustrate, noise signal $V_{noise}$ is attenuated by the air, but since $C_{in+}$ and $C_{in-}$ are generally not equal, $V_{in+,noise}$ and $V_{in-,noise}$ are also not equal. As a result, a differential noise input is produced at the inputs of amplifier 420. In addition, although the capacitance of the air may be on the order of femtofarads, the capacitances $C_{in+}$ and $C_{in-}$ may generally be on the order of nanofarads. As a result, the attenuation factors in Eqns. 1 and 2 may be on the order of $10^{-6}$. For many devices, such a level of attenuation of the noise signal (e.g., resulting in a noise signal of order 1 μV) results in noise far below the level of the signals within the device. However, for sEMG electrode devices the voltages recorded by the electrodes are also generally small (on the order of μV or smaller), so that even the attenuated noise signals are problematic and interfere with the sEMG signals input to the amplifier 420. Moreover, since sEMG devices are often used in environments containing multiple electronic devices (e.g., AC mains devices, computer processors, displays, etc.) multiple sources of such noise can compound this problem.

FIG. 5 depicts an illustrative amplifier 520 of an sEMG device 500 in which a shield 560 is arranged to mitigate interference caused by external noise, according to some embodiments. Shield 560 may be referred to as an "electromagnetic shield" in that it mitigates electromagnetic interference, although it may be appreciated that, in at least some cases, the shield may not interact with both electric and magnetic fields when shielding external sources of interference.

As with the example of FIG. 4, in device 500 an external source of noise 510 produces noise signals $V_{in+,noise}$ and $V_{in-,noise}$ at the inputs to amplifier 520. To reduce the effect of this noise, a shield 560 is arranged between the noise source 510 and the amplifier 520, and is coupled to the user's body 550. Shield 560 produces additional attenuation of the noise signal $V_{noise}$, as described in more detail below. Shield 560 may comprise any suitable conductive material or materials, including, but not limited to, one or more metals and/or alloys (e.g., aluminum, copper, and/or mu-metals), conductive paint (e.g., silver and/or carbon-based paint), conductive fabric (e.g., silver nanowire), conductive polymers (e.g., carbon or graphene filled polylactic acid (PLA)), conductive plastics, conductive rubbers, conductive silicones, or combinations thereof. Shield 560 may also include one or more non-conductive components that may be combined with any one or more conductive components, such as the aforementioned examples.

Based on the illustrated parasitic capacitances of the air ($C_{air}$ and $C'_{air}$), amplifier inputs from electrodes 541 and 543 shown in FIG. 5, and the capacitance $C_{body}$ representing the coupling of the shield 560 to the user's body 550, the voltage signals that the noise source 510 produces as input to the amplifier 520 may be expressed as:

$$V_{in+,noise} = \left(\frac{C'_{air}}{C'_{air} + C_{body}}\right) \times \left(\frac{C_{air}}{C_{air} + C_{in+}}\right) \times V_{noise} \quad \text{(Eqn. 3)}$$

$$V_{in-,noise} = \left(\frac{C'_{air}}{C'_{air} + C_{body}}\right) \times \left(\frac{C_{air}}{C_{air} + C_{in-}}\right) \times V_{noise} \quad \text{(Eqn. 4)}$$

where once again the resistances $R_{body}$, $R_{in+}$, $R_{in0}$, $R_{in-}$ are ignored for simplicity. Electrode 542 of FIG. 5 is connected to circuit ground 524. In at least some cases, the connection of electrode 542 to circuit ground 524 may act to bias the body 550; for example, the connection may stabilize the body DC potential at circuit ground.

The magnitude of $C_{body}$ may be expected to be on the order of nanofarads, and as such the additional attenuation factor of $$\left(\frac{C'_{air}}{C'_{air} + C_{body}}\right)$$

present in Eqns. 3 and 4 compared with the single attenuation factor in Eqns. 1 and 2 leads to a greater attenuation of the noise at the inputs of the amplifier 520 using the circuit configuration shown in the example of FIG. 5.

It will be appreciated that the parasitic capacitances of the air 531 and 532 may not be identical to one another in all cases due to minor differences in environment between the noise source and the shield but is treated as so in the discussion above for simplicity. Similarly, it will be appreciated that the parasitic capacitances of the air 533 and 534 may not be identical to one another in all cases due to minor differences in environment between the shield and the amplifier, but is treated as so in the discussion above for simplicity.

It will be appreciated that shield 560 may be arranged between noise source 510 and the amplifier 520 in numerous ways, and that shield 560 may have any suitable geometry to enable such an arrangement. In some embodiments, shield 560 encloses (e.g., completely surrounds) the amplifier so that the shield is arranged between the amplifier and the external noise sources. In some embodiments, shield 560 may surround the amplifier so that the shield is arranged between the amplifier and noise sources that may be incident on the amplifier from some directions, but where the shield does not completely enclose the amplifier. It will also be appreciated that shield 560 may completely surround or partially surround an entire sEMG system, such as sEMG system 100 shown in FIG. 1.

For example, in the case of the illustrative sEMG device shown in FIGS. 2 and 3, shield 560 may be implemented as a conductive layer that surrounds the sEMG sensors 204 and/or 304 without the shield being located between the sEMG sensors 204 and/or 304 and the wearer's skin. Such an arrangement may enable attenuation of noise by coupling the shield to the wearer's body in any of various ways, examples of which are discussed below.

In addition, while in the example of FIG. 5 the shield 560 is coupled to the wearer's body via sEMG electrode 545, the shield may in general be electrically coupled to the wearer's body in any suitable way using any number of auxiliary conductors (that is, conductors other than sEMG electrodes connected to one or more amplifier inputs of the device). For instance, the shield may be electrically coupled to the wearer's body via one or more electrodes other than an sEMG electrode and/or via one or more other conductors. In some implementations, an auxiliary conductor may be part of the shield itself.

Shield 560 may be electrically coupled to any suitable part or parts of the wearer's body. In the case of an sEMG device configured to be worn on an arm, for example, the shield may be configured to electrically couple to the same arm, including the ventral and/or dorsal sides of the arm, and/or to other parts of the body (e.g., the other arm). The presence of body hair on surface of the body is a complicating factor for achieving a good electrical contact with the body for surface-mounted electrodes. Electrically coupling the shield to the ventral side of the arm may be advantageous, as the ventral side of the arm typically has less body hair than the dorsal side resulting in a better coupling of the shield to the body. It should be appreciated that a desired or optimal placement of the electrode/conductor connected to shield 560 on a user's body may vary from user to user depending on one or more factors including, but not limited to, density of body hair, type of wearable sEMG device, and user preference.

Although the techniques discussed above in relation to FIG. 1, FIG. 2, FIG. 3, FIG. 4 and FIG. 5 are discussed in the context of differential input amplifiers, it will be appreciated that the shielding techniques described herein can also be implemented with other types of amplifiers, such as single-ended input amplifiers, in place of the differential input amplifier in the above-described examples. As may be noted from Eqns. 3 and 4 above, the amplitude of the noise may be attenuated at each individual input of an amplifier, which may also be the case for amplifiers other than differential input amplifiers.

Figure 6A:
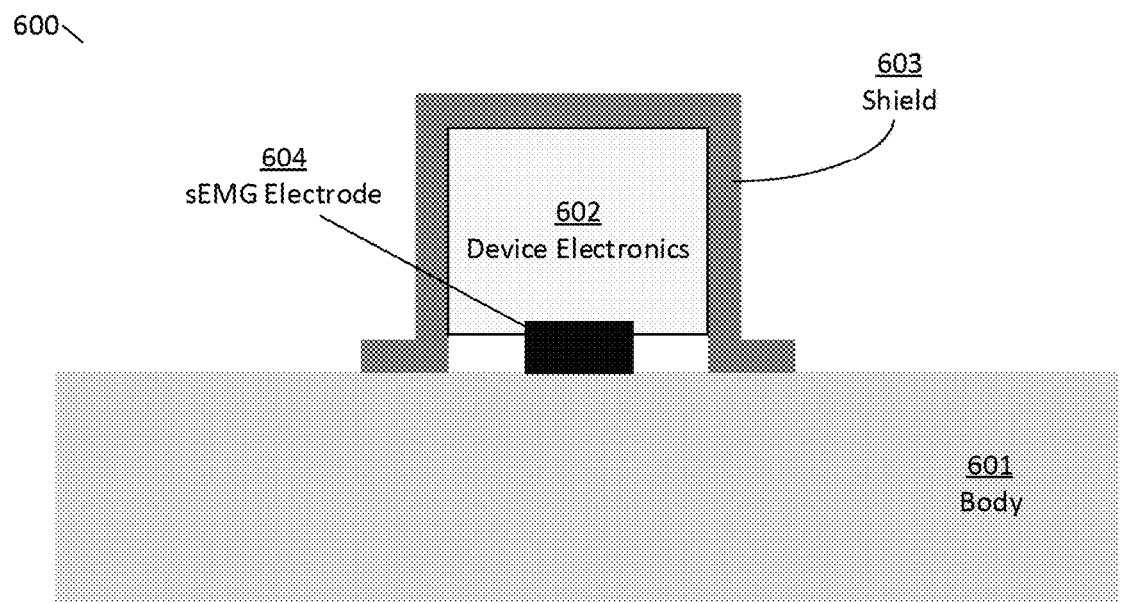
FIGS. 6A-6D depict illustrative cross-sectional views of sEMG devices that include a shield surrounding electronics of the sEMG device, according to some embodiments.
Figure 6B:
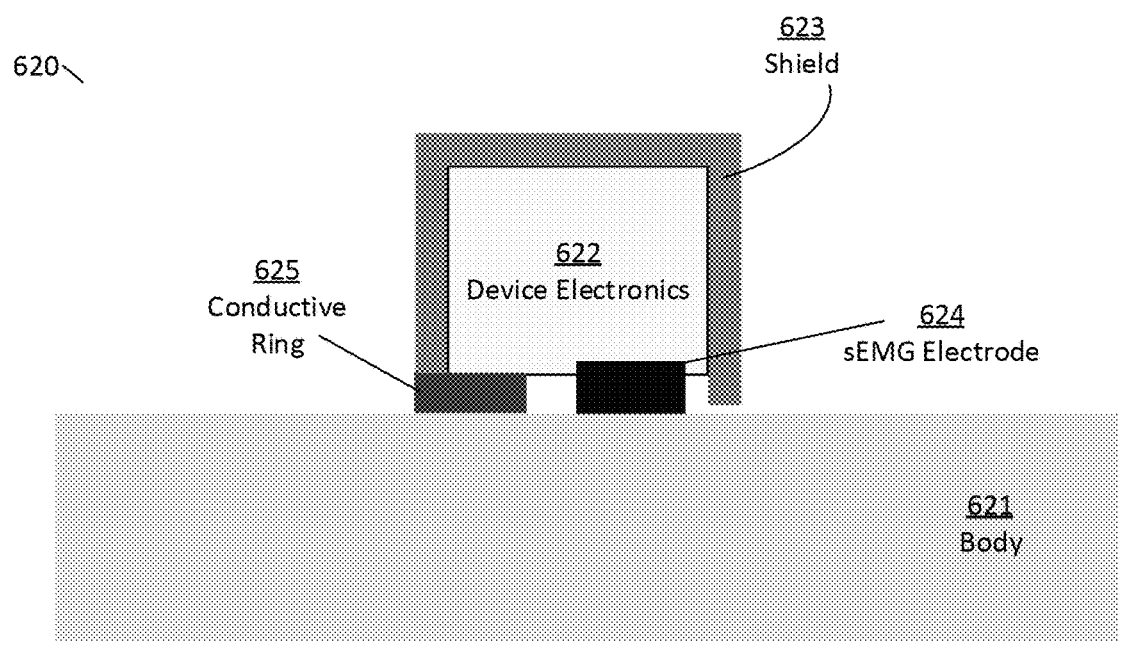
Figure 6C:
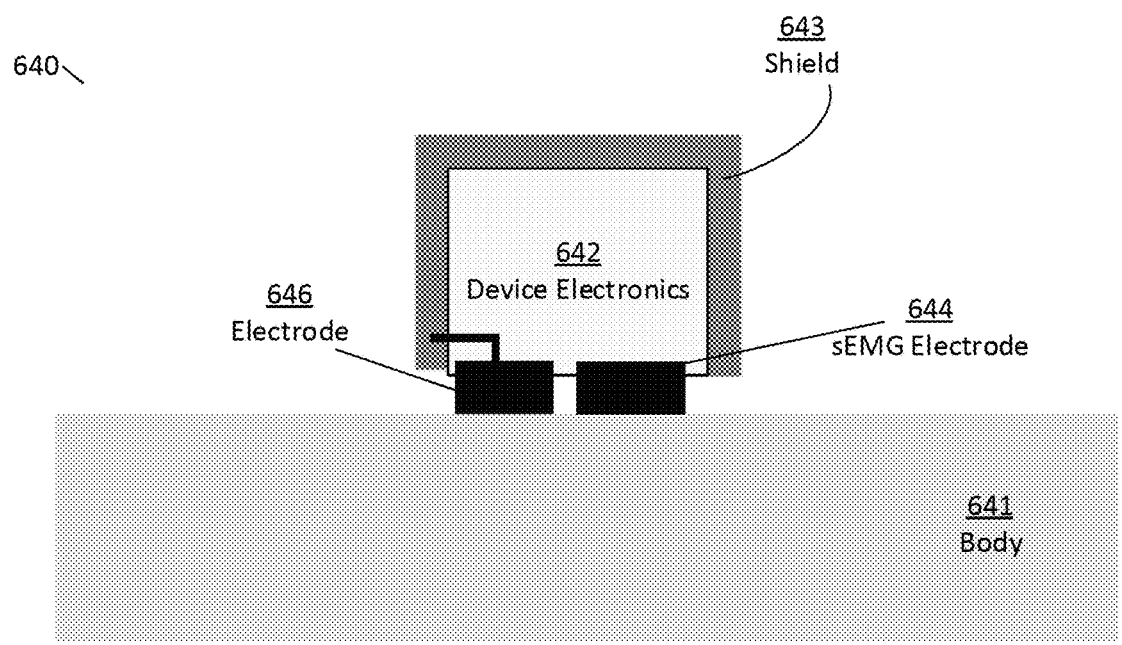

FIGS. 6A-6C depict illustrative cross-sectional views of sEMG devices that include a shield completely or partially surrounding electronics of the sEMG device (e.g., one or more amplifiers or even an entire sEMG system), according to some embodiments. In the example of FIG. 6A, sEMG device 600 includes a shield 603 that surrounds device electronics 602 and an sEMG electrode 604. Shield 603 extends onto the wearer's body 601 to electrically couple the shield to the body as discussed above in relation to FIG. 5. As a result, the shield 603 attenuates external sources of noise (not pictured) that may couple to aspects of the device electronics 602.

According to some embodiments, shield 603 may include and/or may form part of the housing of sEMG device 600. As non-limiting examples, the shield 603 may comprise a rigid conductor that forms a housing around device electronics 602 and contacts the body 601; the shield 603 may comprise a conductive material that is arranged on the exterior, interior and/or embedded within a housing around device electronics 602 such that the conductive material contacts the body 601 (e.g., a conductive paint applied to the housing); and/or the shield 603 may comprise a conductive fabric which may, or may not, be attached to a housing around device electronics 602.

In the example of FIG. 6B, sEMG device 620 includes a shield 623 that surrounds device electronics 622 and an sEMG electrode 624, and further includes a conductive ring 625 (shown in cross section) connected to the shield that electrically couples the shield to the body as discussed above in relation to FIG. 5. As a result, the shield 623 attenuates external sources of noise (not pictured) that may couple to aspects of the device electronics 622. In some embodiments, the conductive ring may be a metal ring that extends partially, or completely, around the body 621 of the wearer.

According to some embodiments, shield 623 may include and/or may form part of the housing of sEMG device 620. As non-limiting examples, the shield 623 may comprise a rigid conductor that forms a housing around device electronics 622 and contacts the body 621; the shield 623 may comprise a conductive material that is arranged on the exterior, interior and/or embedded within a housing around device electronics 622 such that the conductive material contacts the body 621 (e.g., a conductive paint applied to the housing); and/or the shield 623 may comprise a conductive fabric which may, or may not, be attached to a housing around device electronics 622.

In the example of FIG. 6C, sEMG device 640 includes a shield 643 that surrounds device electronics 642 and an sEMG electrode 644, and further includes an electrode 646 connected to the shield that electrically couples the shield to the body as discussed above in relation to FIG. 5. As a result, the shield 643 attenuates external sources of noise (not pictured) that may couple to aspects of the device electronics 642. In some embodiments, the electrode 646 may be an auxiliary conductor, which includes a dry sEMG electrode.

According to some embodiments, shield 643 may include and/or may form part of the housing of sEMG device 640. As non-limiting examples, the shield 643 may comprise a rigid conductor that forms a housing around device electronics 642 and contacts the body 641; the shield 643 may comprise a conductive material that is arranged on the exterior, interior and/or embedded within a housing around device electronics 642 such that the conductive material contacts the body 641 (e.g., a conductive paint applied to the housing); and/or the shield 643 may comprise a conductive fabric which may, or may not, be attached to a housing around device electronics 642.

Figure 6D:
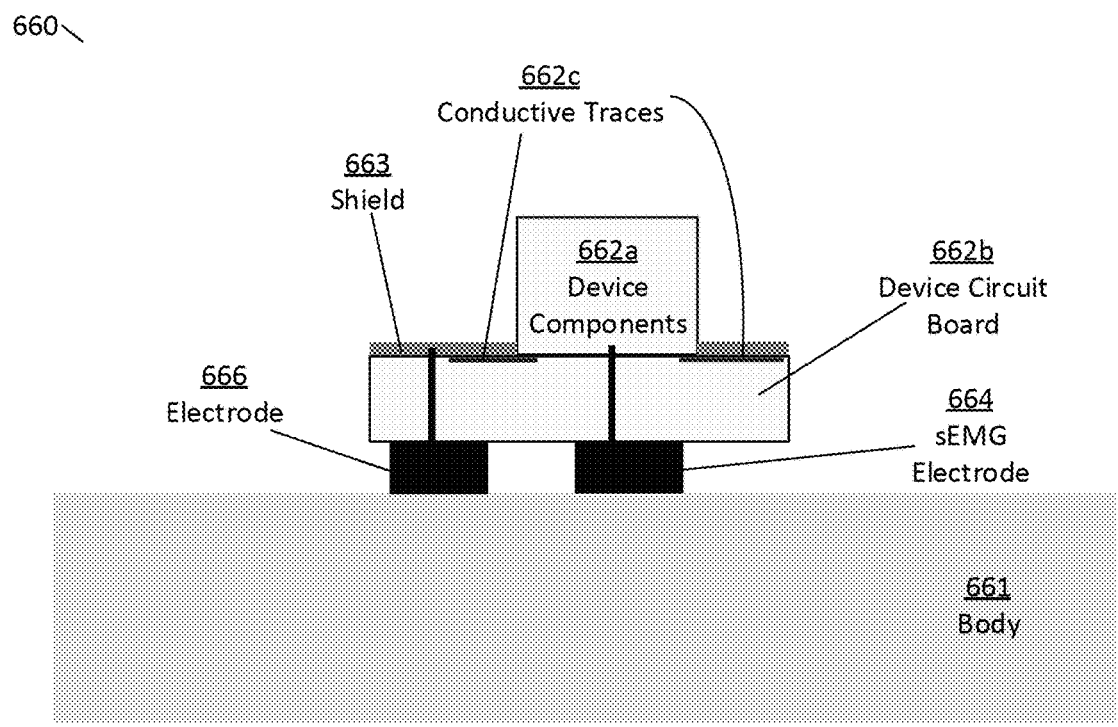

In the example of FIG. 6D, components 662a and circuit board(s) 662b of the device electronics are illustrated as separate elements, with conductive traces 662c of the circuit board 662b also being illustrated. Illustrative sEMG device 660 includes a shield 663 that covers the device circuit board(s) 662b and conductive traces 662c that are routed on the circuit board(s) 662b. The device 660 also includes an sEMG electrode 664 and an electrode 666 connected to the shield that electrically couples the shield to the body as discussed above in relation to FIG. 5. As a result, the shield 663 attenuates external sources of noise (not pictured) that may couple to the conductive traces 662c. In some embodiments, the electrode 666 may be an sEMG electrode. As a non-limiting example, the shield 663 may be implemented as a shielding film layer that is laminated onto the circuit board(s) 662b. In the example of FIG. 6D, therefore, the shield is arranged around part of the device electronics (i.e., the device circuit board 662b), but may not necessarily be arranged around the components 662a of the device electronics in order for the shield to attenuate external sources of noise.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

As used herein, elements referred to as being electrically coupled to one another are arranged such that changes in electrical potential in one element may cause changes in electrical potential in the other element. In this manner, the noise source 510 in the example of FIG. 5 is electrically coupled to the amplifier 520 and to the shield 560. Further, as used herein elements referred to as being electrically connected to one another are arranged so that an electrical conductor directly connects the elements together. For instance, the electrode 545 in the example of FIG. 5 may be electrically connected to the shield 560.

The implementations of DC-coupled amplification circuitry described herein employ discrete analog circuit components. However, it should be appreciated that all or portions of the amplification circuitry and/or associated circuitry in the signal chain may alternatively be implemented using AC-coupled amplification circuitry, one or more application specific integrated circuits (ASICs), and/or any commercial or custom silicon implementation, as embodiments are not limited in this respect. Moreover, it will be appreciated that in some embodiments amplification circuitry may not be included in an sEMG device but rather analog-to-digital converters (ADCs) may directly acquire sEMG signals.

Although the above-discussed examples are discussed in the context of interfaces with EMG sensors, it is understood that the shielding techniques described herein for noise reduction could also be implemented in wearable interfaces with other types of sensors including, but not limited to, electrocardiography (ECG), electroencephalogram (EEG), mechanomyography (MMG) sensors, sonomyography (SMG) sensors, and electrical impedance tomography (EIT) sensors.

Various aspects of the apparatus and techniques described herein may be used alone, in combination, or in a variety of arrangements not specifically discussed in the embodiments described in the foregoing description and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A wearable device comprising:
   amplification circuitry comprising at least a first differential amplifier;
   at least two dry sEMG electrodes electrically connected to the amplification circuitry;
   at least one auxiliary conductor not electrically connected to the amplification circuitry, wherein the at least one auxiliary conductor is configured to be electrically coupled to a wearer of the wearable device; and
   an electromagnetic shield electrically connected to the at least one auxiliary conductor,
   wherein the amplification circuitry is positioned between the electromagnetic shield and the at least two dry sEMG electrodes.

2. The wearable device of claim 1, wherein the electromagnetic shield surrounds at least one input of the first differential amplifier.

3. The wearable device of claim 1, wherein the electromagnetic shield comprises a metal.

4. The wearable device of claim 1, wherein the electromagnetic shield comprises a conductive fabric.

5. The wearable device of claim 1, wherein the electromagnetic shield comprises a conductive paint applied to the at least a portion of the wearable device.

6. The wearable device of claim 1, wherein the electromagnetic shield comprises a conductive tape.

7. The wearable device of claim 1, wherein the electromagnetic shield comprises a conductive plastic.

8. The wearable device of claim 1, wherein the first differential amplifier comprises a field-effect transistor (FET).

9. The wearable device of claim 1, wherein the first differential amplifier is configured to have an input impedance of at least 1 GΩ.

10. The wearable device of claim 1, wherein the at least one auxiliary conductor includes one or more sEMG electrodes.

11. The wearable device of claim 1, wherein the at least one auxiliary conductor includes a conductive cylinder, ring and/or torus.

12. The wearable device of claim 1, further comprising a housing, and wherein the electromagnetic shield is arranged within the housing.

13. The wearable device of claim 1, further comprising a housing, and wherein the electromagnetic shield comprises a conductive paint applied to the housing.

14. The wearable device of claim 1, wherein one or more of the at least two dry sEMG electrodes are configured to pass through at least some portion of the wearer's dermis.

* * * * *

UNITED STATES PATENT AND TRADEMARK OFFICE
CERTIFICATE OF CORRECTION

PATENT NO. : 10,687,759 B2
APPLICATION NO. : 16/424144
DATED : June 23, 2020
INVENTOR(S) : Ning Guo et al.

Page 1 of 1

It is certified that error appears in the above-identified patent and that said Letters Patent is hereby corrected as shown below:

On the Title Page

On page 4, in Column 1, item (56), Other Publications, Line 16, delete "Bgy" and insert -- By --, therefor.

On page 4, in Column 2, item (56), Other Publications, Line 52, delete "Protheses." and insert -- Prosthesis. --, therefor.

On page 5, in Column 1, item (56), Other Publications, Line 3, delete "Biomedial" and insert -- Biomedical --, therefor.

On page 5, in Column 1, item (56), Other Publications, Line 32, delete "Geastures." and insert -- Gestures. --, therefor.

On page 5, in Column 1, item (56), Other Publications, Line 38, delete "seperation." and insert -- separation. --, therefor.

Signed and Sealed this
Eighteenth Day of August, 2020

Andrei Iancu
*Director of the United States Patent and Trademark Office*